(12) United States Patent
Ray et al.

(10) Patent No.: US 6,245,336 B1
(45) Date of Patent: Jun. 12, 2001

(54) PREVENTION AND TREATMENT OF ACETAMINOPHEN TOXICITY WITH GRAPE SEED PROANTHOCYANIDIN EXTRACT

(75) Inventors: Siddhartha D. Ray, Milltown, NJ (US); Debasis Bagchi, Omaha, NE (US)

(73) Assignee: Dry Creek Nutrition, Inc., Modesto, CA (US)

( * ) Notice: Subject to any disclaimer, the term of this patent is extended or adjusted under 35 U.S.C. 154(b) by 0 days.

(21) Appl. No.: 09/267,717

(22) Filed: Mar. 11, 1999

(51) Int. Cl.$^7$ .......................... A61K 35/78; A61K 31/52; A61K 31/16
(52) U.S. Cl. ................... 424/195.1; 514/263; 514/264; 514/629
(58) Field of Search .................... 424/195.1; 514/263, 514/264, 629

(56) References Cited

U.S. PATENT DOCUMENTS

| | | |
|---|---|---|
| 4,307,073 | 12/1981 | Nelson . |
| 4,925,870 | 5/1990 | Gabetta . |
| 5,260,340 | 11/1993 | Baranowitz . |
| 5,474,757 | 12/1995 | Yang . |
| 5,569,458 | * 10/1996 | Greenberg . |
| 5,670,549 | 9/1997 | Baranowitz . |
| 6,086,910 | 7/2000 | Howard et al. . |
| 6,099,854 | 8/2000 | Howard et al. . |

OTHER PUBLICATIONS

Ray et al., FASEB Journal, vol. 12, No. 5, pp. A779, Mar. 20, 1998.*

I.A. Donatus, Cytotoxic and Cytoprotective Activities Curcumin; Effects on Paracetamol–Induced Cytotoxicity, Lipid Peroxidation and Glutathione Depletion in Rat Hepatocytes, Biochemical Pharmacology, Jun. 15, 1990.

* cited by examiner

Primary Examiner—Francisco Prats
Assistant Examiner—Susan D. Coe
(74) Attorney, Agent, or Firm—Marshall, O'Toole, Gerstein, Murray & Borun

(57) ABSTRACT

A method for preventing and/or reducing the toxicity of acetaminophen is disclosed. An amount of grape seed proanthocyanidin extract effective to inhibit toxicity of acetaminophen is administered before, simultaneous with, and/or after dosage of acetaminophen. This allows for increased therapeutic dosages of acetaminophen to be administered with reduced risk of toxic effects, and for prevention of toxic effects in people with special sensitivity to acetaminophen. A composition containing both acetaminophen and grape seed proanthocyanidin extract, allowing for ease of administration of an amount of grape seed proanthocyanidin extract effective to protect from toxicity, also is disclosed.

12 Claims, 5 Drawing Sheets

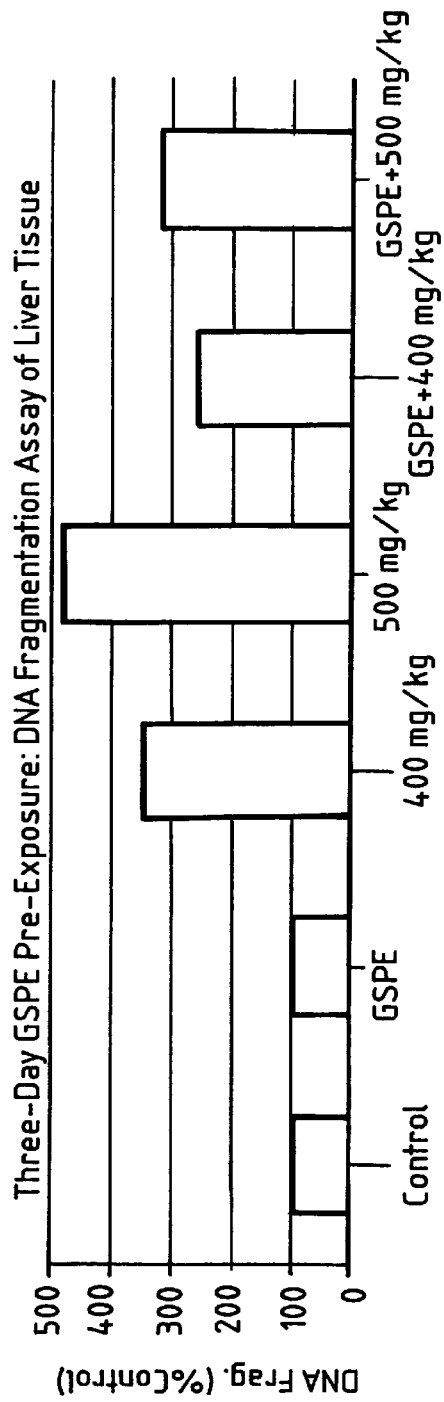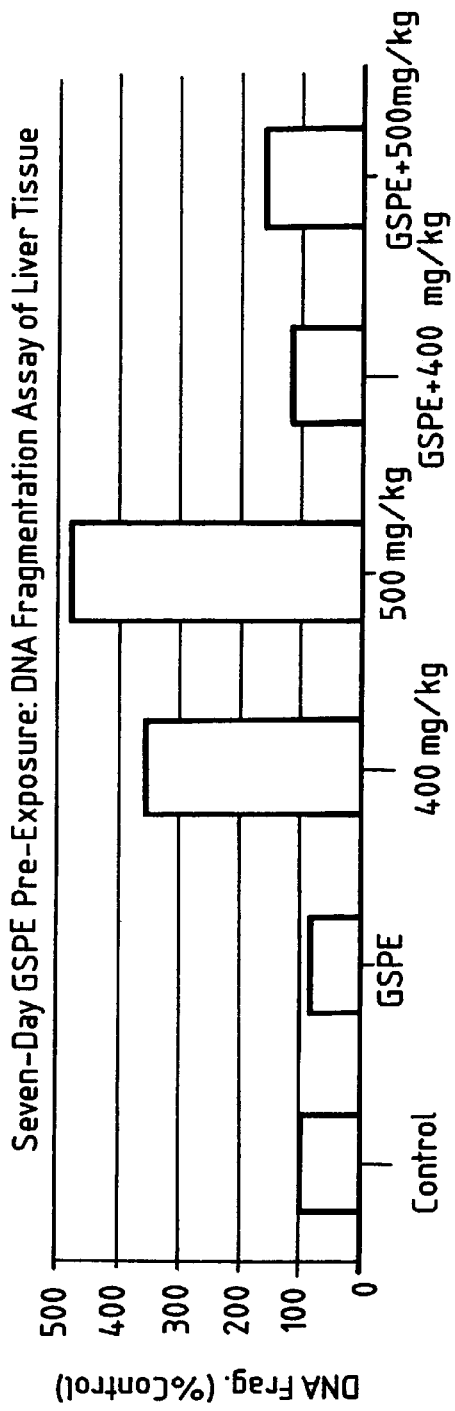

CONTROL

GSPE

ACETAMINOPHEN

GSPE + ACETAMINOPHEN

PREVENTION AND TREATMENT OF ACETAMINOPHEN TOXICITY WITH GRAPE SEED PROANTHOCYANIDIN EXTRACT

BACKGROUND OF THE INVENTION

The invention relates generally to a method and composition for preventing and/or treating acetaminophen toxicity in a person who has received or is receiving an excessive amount of acetaminophen.

Acetaminophen, or N-acetyl-p-amino phenol,

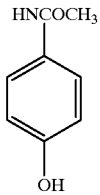

is a well-known and reliable analgesic commonly used and available without prescription in the United States. Acetaminophen can cause serious damage to liver cells and tissues when an excessive amount is taken. The amount that can lead to this damage varies for individuals based on various factors; for example, lower body weight, past alcoholism, ingestion of acetaminophen with alcohol, or other special sensitivity all can lead to damage from ingestion of amounts of acetaminophen normally not excessive. According to the United States Poison Control Center, thousands of cases of acetaminophen toxicity are reported in the U.S. each year.

Acetaminophen is thought to be metabolized in the liver by cytochrome P-450 enzymes, resulting in highly reactive oxygen free radicals and toxic metabolites, e.g., N-acetyl-p-benzoquinone imine. These metabolites interact with cellular lipids, protein, DNA, and biological macromolecules, causing cell injury and death. When acetaminophen is taken in a non-excessive amount, these metabolites are cleared by hepatic glutathione stores. Excessive amounts of acetaminophen are thought to deplete these glutathione stores, resulting in hepatic necrosis.

Present methods of treating acetaminophen overdose include induction of vomiting, stomach lavage, and/or administration of acetylcysteine to replenish hepatic glutathione. These methods, while somewhat effective in preventing injury if performed within 24 hours of ingestion of the excess amount, are not preventative measures that can inhibit toxicity from the initial time of ingestion. These methods also usually require assistance of medical personnel, which might not be immediately available, particularly because acetaminophen is available for use without a prescription.

There remains a need for an effective method to prevent and/or reduce acetaminophen toxicity in a convenient manner, without need for medical supervision or assistance. The present invention fulfills this need and provides further related advantages.

SUMMARY OF THE INVENTION

The present invention resides in a method to prevent and/or reduce the effects of acetaminophen toxicity by administering grape seed proanthocyanidin extract (GSPE) to a person in an amount effective to counteract the toxic effects of the acetaminophen, preferably from about 0.1 to about 3 mg of GSPE per kg of body weight. The invention also allows for regular supplementation with GSPE as a prophylactic to protect against acetaminophen toxicity. The GSPE may be administered by various methods, such as orally, intravenously, and intramuscularly, and may be administered before, during, and/or after ingestion of acetaminophen. The present invention is also embodied in a composition comprising acetaminophen and GSPE in sufficient quantity to inhibit acetaminophen toxicity for the amount present in the composition is provided.

Other features and advantages of the present invention should become apparent from the following detailed description of the invention, taken with the illustrative drawings, which illustrate the principles of the invention.

BRIEF DESCRIPTION OF THE DRAWINGS

FIG. 5 is a graphical representation of the DNA fragmentation in assays of liver tissue of mice treated with acetaminophen and GSPE, after a three-day exposure to GSPE.

FIG. 6 is a graphical representation of the DNA fragmentation in assays of liver tissue of mice treated with acetaminophen and GSPE, after a seven-day exposure to GSPE.

DETAILED DESCRIPTION OF THE INVENTION

Grape seed proanthocyanidins are natural antioxidants known to have a broad spectrum of biological, pharmacological, and chemoprotective properties against free radicals and oxidative stress. The novel grape seed proanthocyanidin extract (GSPE) ActiVin™ IH636, is a highly bioavailable form of GSPE. High-pressure liquid chromatography-mass spectrometry and gas chromatography-mass spectrometry studies indicate that the GSPE contains monomeric- dimeric-, trimeric-, tetrameric, oligomeric-, and polymeric proanthocyanidins, as well as tannin. The present invention involves administering GSPE to a person who has received or is receiving an excessive amount of acetaminophen. GSPE can be administered either before, simultaneous with, and/or after ingestion of the acetaminophen. Current studies suggest that GSPE may block major pathways of acetaminophen-induced liver toxicity. The effective amount of GSPE is believed to range from about 10 to about 200 mg of GSPE per day for a 70 kg human, or from about 0.1 to about 3 mg GSPE/kg body weight.

EXAMPLES

Trials of the efficacy of GSPE in preventing acetaminophen toxicity were performed using mice as test subjects.

The GSPE used in the subject trials is a standardized water-ethanol extract from red grape seeds, identified as IH636 by InterHealth Nutraceuticals, Inc., of Concord, Calif. The dosage used in the subject trials was 100 mg of GSPE per kg of body weight, daily for three or seven days. This dosage is equivalent to about 40 mg of GSPE per day for a 70 kg human, or about 0.6 mg GSPE/kg of body weight, based on the following formula from the *CRC Handbook of Toxicology*, Delanko M. J. and Hollinger M. A. eds., CRC Press 1995, p. 654:

Human Dose Equivalency=Animal Dose×(Human Body Weight/Animal Body Weight)$^{1/3}$ GSPE was dissolved in phosphate-buffered saline solution and the solution was administered orally. Acetaminophen then was administered intraperitoneally, as a single toxic dose, in dosage of either 400 or 500 mg/kg. These dosage levels are equivalent to approximately 10 grams for normal healthy adults and 4 to 6 grams for alcoholics, levels that have been found toxic for humans. Twenty-four hours after administration of the acetaminophen, blood samples were removed from the subjects and analyzed for serum alanine aminotransferase activity, a well-known biomarker of liver toxicity. Liver samples also were taken and analyzed them for apoptotic and necrotic cell death DNA damage and gene expression.

Figure 1:
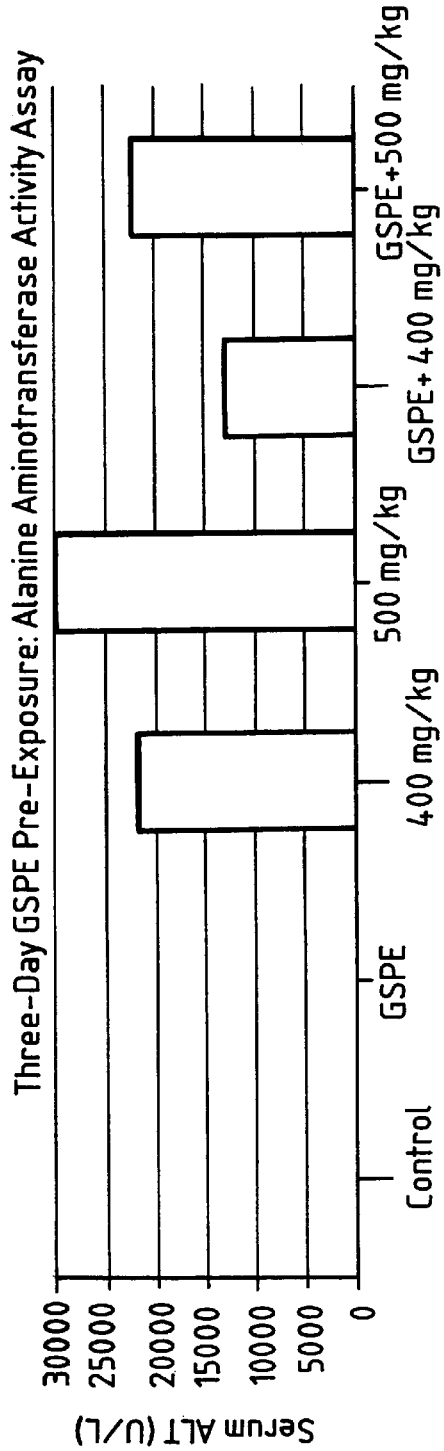
FIG. 1 is a graphical representation of the alanine aminotransferase activity of mice treated with acetaminophen and grape seed proanthocyanidin extract (GSPE), after a three-day exposure to GSPE.
Figure 2:
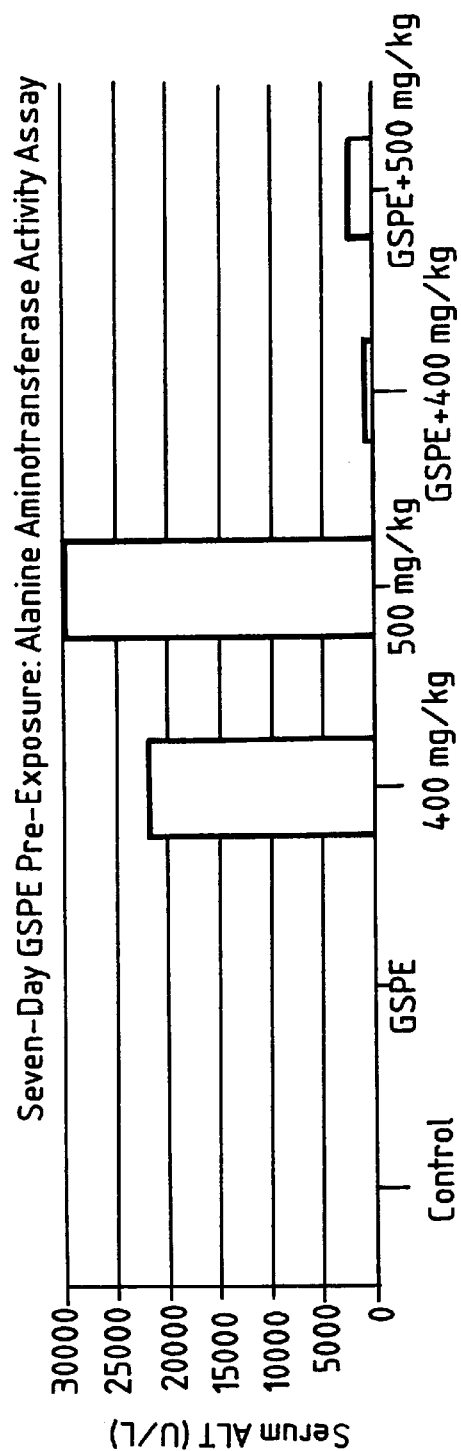
FIG. 2 is a graphical representation of the alanine aminotransferase activity of mice treated with acetaminophen and GSPE, after a seven-day exposure to GSPE.

Results of the study show that short-term (three-day) pre-exposure to GSPE provided partial protection, while long-term (seven-day) exposure to GSPE provided near total protection, against acetaminophen-induced liver toxicity in all the parameters studied. As shown in FIGS. 1 and 2, alanine aminotransferase activity (ALT) was reduced for test subjects receiving GSPE prior to administration of acetaminophen. FIGS. 1 and 2 show that serum ALT was about 22,000 U/L for test subjects receiving 400 mg/kg of acetaminophen with no pre-exposure to GSPE, and about 30,000 U/L for test subjects receiving 500 mg/kg of acetaminophen with no pre-exposure to GSPE. FIG. 1 shows that three-day pre-exposure to GSPE reduced these serum ALT levels to about 13,500 and 22,500 U/L, respectively. FIG. 2 shows that seven-day pre-exposure to GSPE reduced these serum ALT levels to about 1,000 and 2,500 U/L, respectively.

Figure 3:
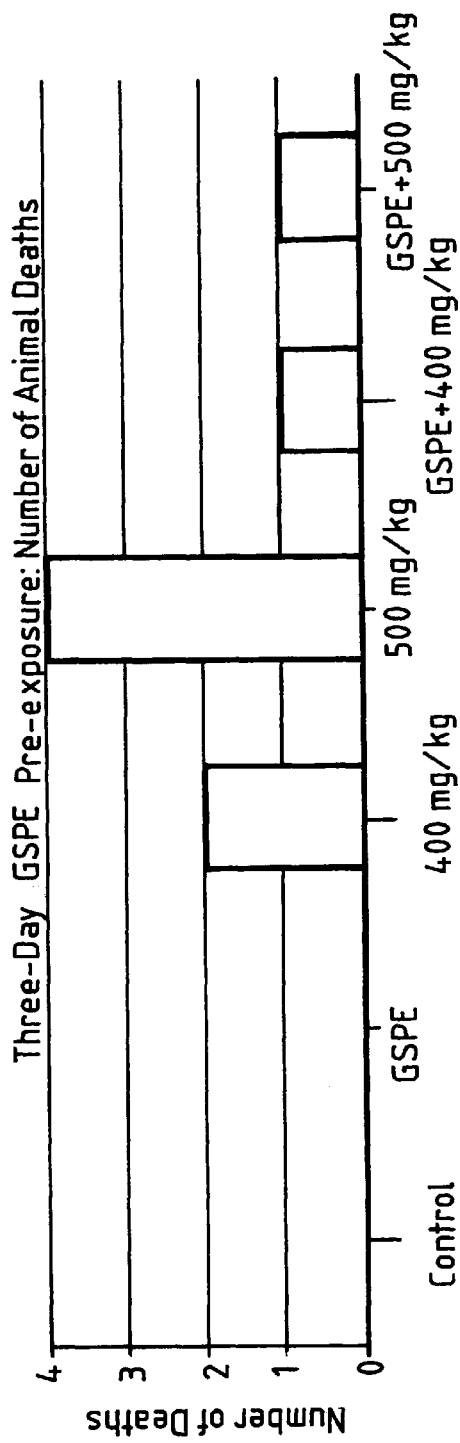
FIG. 3 is a graphical representation of the number of deaths of mice treated with acetaminophen and GSPE, after a three-day exposure to GSPE.
Figure 4:
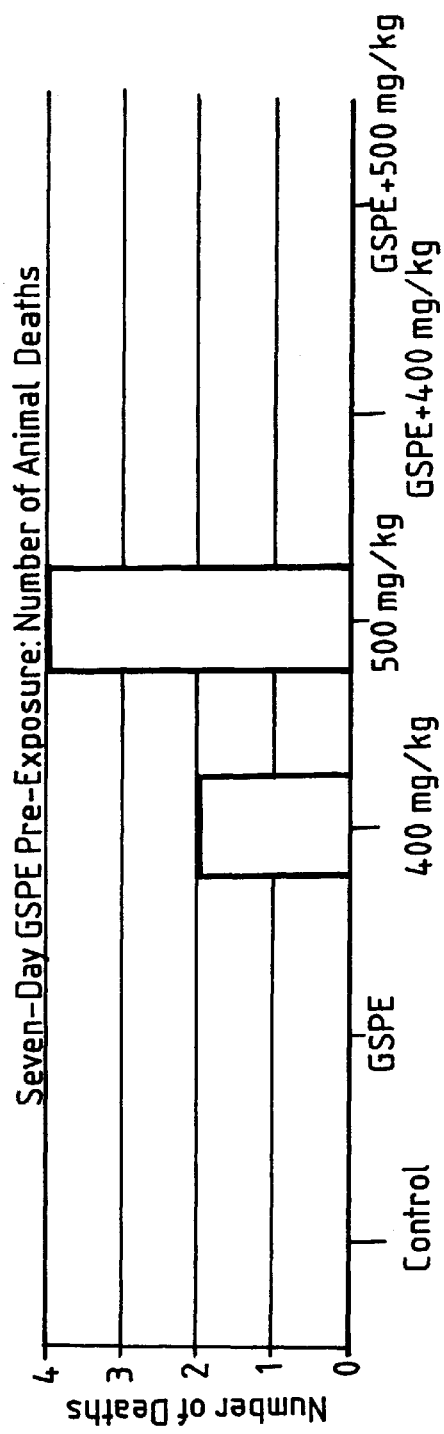
FIG. 4 is a graphical representation of the number of deaths of mice treated with acetaminophen and GSPE, after a seven-day exposure to GSPE.

FIGS. 3 and 4 show that the number of deaths of test subjects was reduced by administration of GSPE prior to administration of acetaminophen. Without pre-exposure to GSPE, 2 of the test subjects receiving 400 mg/kg and 4 of the test subjects receiving 500 mg/kg of acetaminophen died. FIG. 3 shows that three-day pre-exposure to GSPE reduced the number of deaths in each dosage group to 1. FIG. 4 shows that seven-day pre-exposure to GSPE reduced the number of deaths in each dosage group to 0.

In addition, the results of DNA fragmentation assays from liver tissue set forth in FIGS. 5 and 6 show that acetaminophen-induced DNA fragmentation was significantly reduced. Without pre-exposure to GSPE, the amount of DNA fragmentation was about 3.5 times that of the control group among the test subjects receiving 400 mg/kg and about 4.8 times that of the control group among the test subjects receiving 500 mg/kg of acetaminophen. FIG. 5 shows that with three-day pre-exposure to GSPE, the amounts of DNA fragmentation fell to about 2.7 and 3.4 times that of the control group, respectively. FIG. 6 shows that with seven-day pre-exposure to GSPE, the amounts of DNA fragmentation fell to about 1.2 and 1.6 times that of the control group, respectively.

Figure 7:
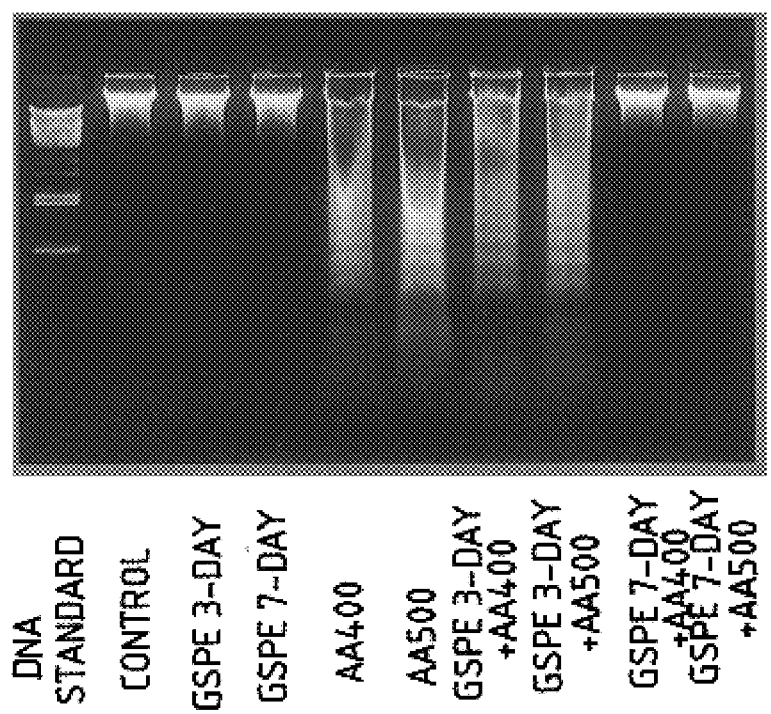
FIG. 7 shows the results of agarose gel electrophoresis of DNA from mice treated with acetaminophen and GSPE.
Figure 8:
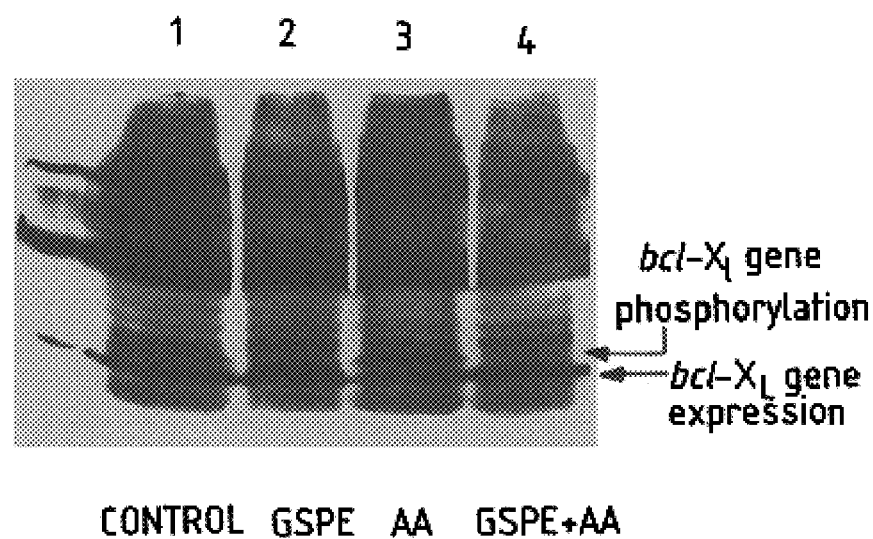
FIG. 8 shows the results of Westren blot analysis of liver proteins from mice treated with acetaminophen and GSPE.
Figure 9:
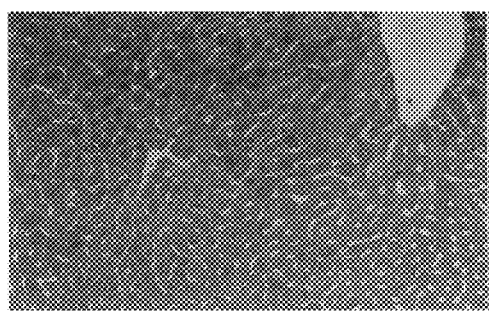
FIGS. 9–12 are photographs of slides showing liver sections from mice treated with acetaminophen and GSPE indicating cell structure.
Figure 10:
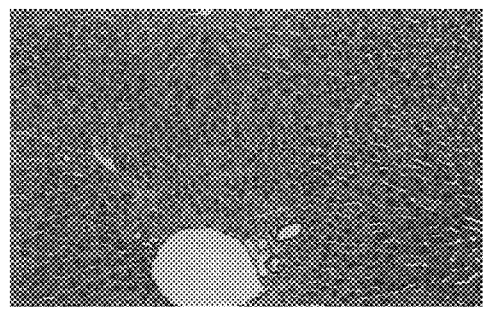
Figure 11:
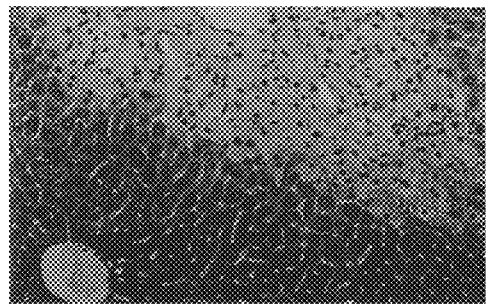
Figure 12:
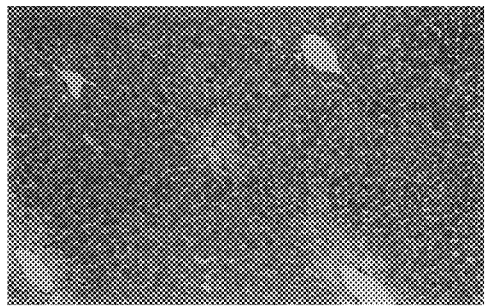

FIG. 7 shows the results of agarose gel electrophoresis for DNA from the test subjects, in which increased DNA fragmentation is indicated by the white area. The results show less DNA fragmentation in the tissue from subjects receiving acetaminophen and GSPE than in those receiving acetaminophen alone. In addition, the results of a Westren blot analysis of liver proteins from the test subjects depicted in FIG. 8 show that GSPE enhances the expression of bcl-$X_L$, a death inhibitory gene (as shown by the darker bcl-$X_L$ gene expression band in Lane 3), and inhibits acetaminophen-induced phosphorylation of the bcl-$X_L$ gene (as shown by the absence of the bcl-X gene phosphorylation band in Lane 3). FIGS. 9 through 12 show comparison liver sections from test subjects at 400× magnification. FIGS. 9 and 10 show normal liver sections from test subjects not given acetaminophen. Exposure to acetaminophen without GSPE leads whitening and browning of cells, indicating toxicity. This whitening is apparent as the lighter and darker regions of tissue in FIG. 11, which shows a liver section from a test subject given 500 mg/kg body weight of acetaminophen, without pre-treatment with GSPE. FIG. 12 shows a liver section from a test subject given seven-day pretreatment with GSPE prior to being given 500 mg/kg body weight of acetaminophen, in which this apparent lightening and darkening is sharply reduced.

The results of the study indicate that GSPE is effective in reducing the toxic effects of acetaminophen. GSPE administration is therefore useful, for example, in allowing persons to take higher doses of acetaminophen, and receive the subsequently greater therapeutic benefit without the severe risk of suffering from its toxic effects. GSPE is also useful for preventing damage to individuals who have a special sensitivity to the toxic effects of acetaminophen, such as alcoholics.

In the study described above, GSPE was administered prior to dosage of acetaminophen. Similar effects in preventing acetaminophen-induced toxicity are achieved if GSPE is administered simultaneous with, or shortly after, ingestion of acetaminophen. GSPE is delivered orally in saline solution, either immediately or 12 hours after administration of a toxic dose of acetaminophen intraperitoneally to the test subjects, as was done in the previous example. Blood and liver samples are taken 24 hours after the administration of acetaminophen, to verify reduced damage liver and DNA damage.

An embodiment of the invention that provides for simultaneous dosage of acetaminophen and GSPE is a composition of acetaminophen and sufficient GSPE to reduce acetaminophen toxicity, thereby conveniently and effectively reducing chance of toxic dosage. The pharmaceutical compositions according to this embodiment of the invention can be in any convenient form suited to the intended mode of administration such as, for example, tablet, capsule or liquid form. The composition can include inert ingredients or diluents, such talc or starch, and it can include additional active pharmaceutical ingredients typically found in cold and flu remedies, such as acetylsalicylic acid or caffeine, provided that adverse chemical reactions do not occur as a result of the combination. Preferably, the composition includes a barrier coating between active ingredients. The coating can be made of one of the standard inert compounds used for such coatings, such as food glaze.

The convenience of this embodiment is particularly useful because acetaminophen, available without prescription, is often taken without guidance from a physician as to its potential toxicity. Supplementation of acetaminophen with GSPE can reduce the need for medical consultation, and provides increased safety for non-prescription use of acetaminophen.

Although the invention has been disclosed in detail with reference only to the preferred embodiments, those skilled in the art will appreciate that additional methods of administering GSPE, both separately and in a composition containing acetaminophen, can be made without departing from the scope of the invention. Accordingly, the invention is defined only by the following claims.

We claim:

1. A method for preventing or reducing the toxicity of acetaminophen to a person who has ingested an excessive quantity of acetaminophen, the method comprising administering grape seed proanthocyanidin extract to the person in an amount effective to prevent or reduce the toxicity of the excessive quantity of acetaminophen.

2. A method as defined in claim 1, wherein the amount of grape seed proanthocyanidin extract administered in the step of administering ranges from about 0.1 to about 3 mg/kg of body weight.

3. A method as defined in claim 1, wherein the step of administering grape seed proanthocyanidin extract occurs before the ingestion of the acetaminophen.

4. A method as defined in claim 1, wherein the step of administering grape seed proanthocyanidin extract occurs simultaneously with the ingestion of the acetaminophen.

5. A method as defined in claim 4, wherein the step of administering grape seed proanthocyanidin extract includes a step of administering a composition containing both acetaminophen and grape seed proanthocyanidin extract.

6. A method as defined in claim 1, wherein the step of administering grape seed proanthocyanidin extract occurs after the ingestion of the acetaminophen.

7. A method as defined in claim 1, wherein the step of administering grape seed proanthocyanidin extract is performed orally.

8. A method as defined in claim 1, wherein the step of administering grape seed proanthocyanidin extract is perform intravenously.

9. A method as defined in claim 1, wherein the step of administering grape seed proanthocyanidin extract is performed intramuscularly.

10. A composition comprising:

a) acetaminophen, and b) grape seed proanthocyanidin extract.

11. A composition as defined in claim 10, wherein the composition consists essentially of:

a) acetaminophen, and b) grape seed proanthocyanidin extract.

12. A composition as defined in claim 10, wherein the amount of grape seed proanthocyanidin extract is sufficient to prevent or reduce the toxic effects of the amount of acetaminophen in the composition.

* * * * *

UNITED STATES PATENT AND TRADEMARK OFFICE
CERTIFICATE OF CORRECTION

PATENT NO. : 6,245,336 B1  
DATED : June 12, 2001  
INVENTOR(S) : Ray et al.

Page 1 of 1

It is certified that error appears in the above-identified patent and that said Letters Patent is hereby corrected as shown below:

<u>Title page,</u>
Line 5, replace "Siddhartha" with -- Sidhartha --.

Signed and Sealed this

Twenty-sixth Day of February, 2002

Attest:

Attesting Officer

JAMES E. ROGAN
Director of the United States Patent and Trademark Office